(12) United States Patent
Termanini

(10) Patent No.: US 11,090,163 B1
(45) Date of Patent: Aug. 17, 2021

(54) INTERLOCKING REVERSE HIP PROSTHESIS WITH REMOVABLE TAPERED CENTRAL POST

(71) Applicant: Zafer Termanini, Port Saint Lucie, FL (US)

(72) Inventor: Zafer Termanini, Port Saint Lucie, FL (US)

( * ) Notice: Subject to any disclaimer, the term of this patent is extended or adjusted under 35 U.S.C. 154(b) by 0 days.

(21) Appl. No.: 17/145,332

(22) Filed: Jan. 9, 2021

(51) Int. Cl.
| | | |
|---|---|---|
| *A61F 2/36* | (2006.01) |
| *A61F 2/34* | (2006.01) |
| *A61F 2/46* | (2006.01) |
| *A61L 27/16* | (2006.01) |
| *A61F 2/30* | (2006.01) |
| *A61F 2/32* | (2006.01) |

(52) U.S. Cl.
CPC .............. *A61F 2/34* (2013.01); *A61F 2/3609* (2013.01); *A61F 2/4607* (2013.01); *A61L 27/16* (2013.01); *A61F 2002/3042* (2013.01); *A61F 2002/3069* (2013.01); *A61F 2002/30113* (2013.01); *A61F 2002/30224* (2013.01); *A61F 2002/30383* (2013.01); *A61F 2002/30565* (2013.01); *A61F 2002/3208* (2013.01); *A61F 2002/3401* (2013.01); *A61F 2002/3406* (2013.01); *A61F 2002/3483* (2013.01); *A61F 2002/3611* (2013.01); *A61F 2002/4681* (2013.01)

(58) Field of Classification Search
CPC .. A61F 2/34; A61F 2/4081; A61F 2002/4085; A61F 2/4014; A61F 2/40; A61F 2/4609; A61F 2/4607; A61F 2002/30329; A61F 2002/30331; A61F 2002/30332; A61F 2002/30345; A61F 2002/30349; A61F 2002/3035; A61F 2002/30649; A61F 2002/3065; A61F 2002/30652; A61F 2002/30654; A61F 2/3609; A61F 2002/3615; A61F 2002/365
See application file for complete search history.

(56) References Cited

U.S. PATENT DOCUMENTS

| | | | | | |
|---|---|---|---|---|---|
| 4,632,111 | A | * | 12/1986 | Roche | A61F 2/4609 606/53 |
| 5,061,270 | A | * | 10/1991 | Aboczky | A61F 2/4609 606/91 |
| 5,169,399 | A | * | 12/1992 | Ryland | A61F 2/4609 606/91 |
| 5,171,243 | A | * | 12/1992 | Kashuba | A61F 2/4609 606/86 R |
| 5,171,313 | A | * | 12/1992 | Salyer | A61F 2/4609 606/86 R |

(Continued)

*Primary Examiner* — Alvin J Stewart
(74) *Attorney, Agent, or Firm* — Samir Termanini, Esq.

(57) ABSTRACT

An interlocking reverse hip prosthesis including an acetabular cup having an opening in the central portion of the cup being implanted in the acetabular cavity. The opening has a circular extending wall protruding into the concave portion of the cup a distance at least equal to the diameter of the opening. The inward extension of the cup provides a female Morse taper suited for receiving the male Morse tapered post of the acetabular ball. After implantation of the acetabular cup, the surgeon can easily secure the cup to the acetabular bone using several screws without the interference of the central peg (as in prior implants). The femoral ball is then attached to the cup via central Morse taper.

12 Claims, 5 Drawing Sheets

(56) References Cited

U.S. PATENT DOCUMENTS

| | | | | |
|---|---|---|---|---|
| 5,417,696 A * | 5/1995 | Kashuba | A61F 2/34 | 606/91 |
| 5,540,697 A * | 7/1996 | Rehmann | A61F 2/4609 | 606/91 |
| 5,928,287 A * | 7/1999 | Keller | A61F 2/4609 | 623/22.21 |
| 5,954,727 A * | 9/1999 | Collazo | A61F 2/4609 | 606/91 |
| 6,063,124 A * | 5/2000 | Amstutz | A61F 2/34 | 623/22.21 |
| 7,682,363 B2 * | 3/2010 | Burgi | A61F 2/4609 | 606/91 |
| 7,727,282 B2 * | 6/2010 | Slone | A61F 2/4637 | 623/22.12 |
| 8,021,370 B2 * | 9/2011 | Fenton | A61F 2/34 | 606/91 |
| 8,475,465 B2 * | 7/2013 | Teeny | A61F 2/4609 | 606/99 |
| 8,840,676 B2 * | 9/2014 | Belew | A61F 2/4684 | 623/22.15 |
| 8,920,510 B2 * | 12/2014 | Forsell | A61F 2/34 | 623/22.15 |
| 9,700,418 B2 * | 7/2017 | Melozzi | A61F 2/32 | |
| 10,507,114 B2 * | 12/2019 | Melozzi | A61F 2/3609 | |
| 10,596,011 B2 * | 3/2020 | Beck | A61F 2/4607 | |
| 2006/0069443 A1 * | 3/2006 | Deffenbaugh | A61F 2/4081 | 623/19.11 |
| 2006/0241781 A1 * | 10/2006 | Brown | A61F 2/34 | 623/23.43 |
| 2007/0173856 A1 * | 7/2007 | Parker | A61F 2/34 | 606/99 |
| 2007/0219562 A1 * | 9/2007 | Slone | A61F 2/34 | 606/99 |
| 2007/0250066 A1 * | 10/2007 | Fenton | A61F 2/34 | 606/91 |
| 2008/0255672 A1 * | 10/2008 | Gil | A61F 2/34 | 623/22.28 |
| 2009/0210067 A1 * | 8/2009 | Meridew | A61F 2/34 | 623/22.24 |
| 2010/0131073 A1 * | 5/2010 | Meridew | A61F 2/34 | 623/22.28 |
| 2010/0256771 A1 * | 10/2010 | Roberts | A61F 2/34 | 623/22.36 |
| 2011/0130763 A1 * | 6/2011 | Aux Epaules | A61F 2/4609 | 606/91 |
| 2011/0208202 A1 * | 8/2011 | Zumsteg | A61F 2/4684 | 606/91 |
| 2011/0218637 A1 * | 9/2011 | Termanini | A61F 2/40 | 623/22.15 |
| 2012/0053592 A1 * | 3/2012 | Burgi | A61F 2/4609 | 606/91 |
| 2012/0116533 A1 * | 5/2012 | Forsell | A61F 2/34 | 623/23.11 |
| 2012/0136361 A1 * | 5/2012 | Aux Epaules | A61F 2/4609 | 606/91 |
| 2012/0184965 A1 * | 7/2012 | Burgi | A61F 2/4609 | 606/99 |
| 2012/0271425 A1 * | 10/2012 | Maurer | A61F 2/4609 | 623/19.12 |
| 2013/0079785 A1 * | 3/2013 | Burgi | A61F 2/4609 | 606/91 |
| 2013/0226186 A1 * | 8/2013 | Burgi | A61F 2/4609 | 606/91 |
| 2013/0282133 A1 * | 10/2013 | Krebs | A61F 2/4609 | 623/22.38 |
| 2014/0081283 A1 * | 3/2014 | Liang | A61F 2/4609 | 606/99 |
| 2014/0135777 A1 * | 5/2014 | Cannell | A61F 2/4609 | 606/91 |
| 2014/0156011 A1 * | 6/2014 | Termanini | A61F 2/3609 | 623/19.12 |
| 2014/0200675 A1 * | 7/2014 | Termanini | A61F 2/3609 | 623/23.13 |
| 2014/0336778 A1 * | 11/2014 | Termanini | A61F 2/34 | 623/22.36 |
| 2015/0127113 A1 * | 5/2015 | Termanini | A61B 17/1746 | 623/22.12 |
| 2017/0035571 A1 * | 2/2017 | Loffredo | A61F 2/3603 | |
| 2018/0193156 A1 * | 7/2018 | Zajac | A61F 2/4609 | |
| 2018/0333265 A1 * | 11/2018 | Termanini | A61F 2/3609 | |
| 2019/0151117 A1 * | 5/2019 | Termanini | A61F 2/4609 | |

* cited by examiner

INTERLOCKING REVERSE HIP PROSTHESIS WITH REMOVABLE TAPERED CENTRAL POST

BACKGROUND OF THE INVENTION

The present invention relates to a hip prosthesis and more specifically to an interlocking reverse hip prosthesis with an acetabular component having a removable central Morse tapered central peg for facilitating the insertion of multiple fixation acetabular screws.

While it can be appreciated that several hip implants have commonly been in use for years there is a need for a design which facilitates the insertion of multiple fixation screws at different angles without interference with the central post.

SUMMARY OF THE INVENTION

The present invention provides a new interlocking reverse hip prosthesis with an acetabular ball and central post constructed as one piece. The post is solidly and concentrically attached to a central apical circular opening in an acetabular cup and secured via Morse taper. The acetabular cup is implanted and impacted in an acetabular socket constructed by the surgeon in pelvic bone and is firmly secured by one or more interlocking screws through one or more openings in the acetabular cup. In some embodiments, these interlocking screws are replaced by biocompatible resorbable studs. Subsequently, the central post is inserted into the central apical opening and firmly impacted and held in position via a Morse taper. The femoral component is then inserted and impacted into the femoral medullary canal which has been prepared and hollowed by the surgeon using appropriate size reamers. Note, insertion of multiple interlocking screws is facilitated by the removal of the central post which can interfere with the insertion of the screws at the appropriate angle. During ambulation, the articular femoral cup edge or lip will glide conformably concentrically into the interlocking space which is located between the acetabular ball and the acetabular cup. As will be apparent to those having skill in the art, the geometrical configuration of the present invention makes it very difficult for the femoral cup to dislocate when the range of motion increases since it becomes constrained in the locking space between the acetabular cup and the acetabular ball.

Furthermore, since the articulating surfaces of the two components are fully in contact 100% of the time, it is clear that this will improve the weight distribution and decrease the wear of the surfaces in contact and reduce the number of wear particles released in the joint. The latter, being very detrimental to the proper function of the joint, often leads to osteolysis and loosening of the implant components. A novel feature of this invention is that the Central post is removable and will not impinge or interfere mechanically with the insertion of the interlocking fixation screws. This results in a new reverse hip implant which is not anticipated, rendered obvious, suggested, or even implied by any prior hip prosthesis when considered alone or in any combination.

BRIEF DESCRIPTION OF THE DRAWINGS

Various other object, features and advantages of the present invention will become fully appreciated as the same becomes better understood when considered in conjunction with the current accompanying drawings, in which like reference characters designate the same or similar elements throughout the several views, and wherein.

DETAILED DESCRIPTION OF THE INVENTION

Figure 1:
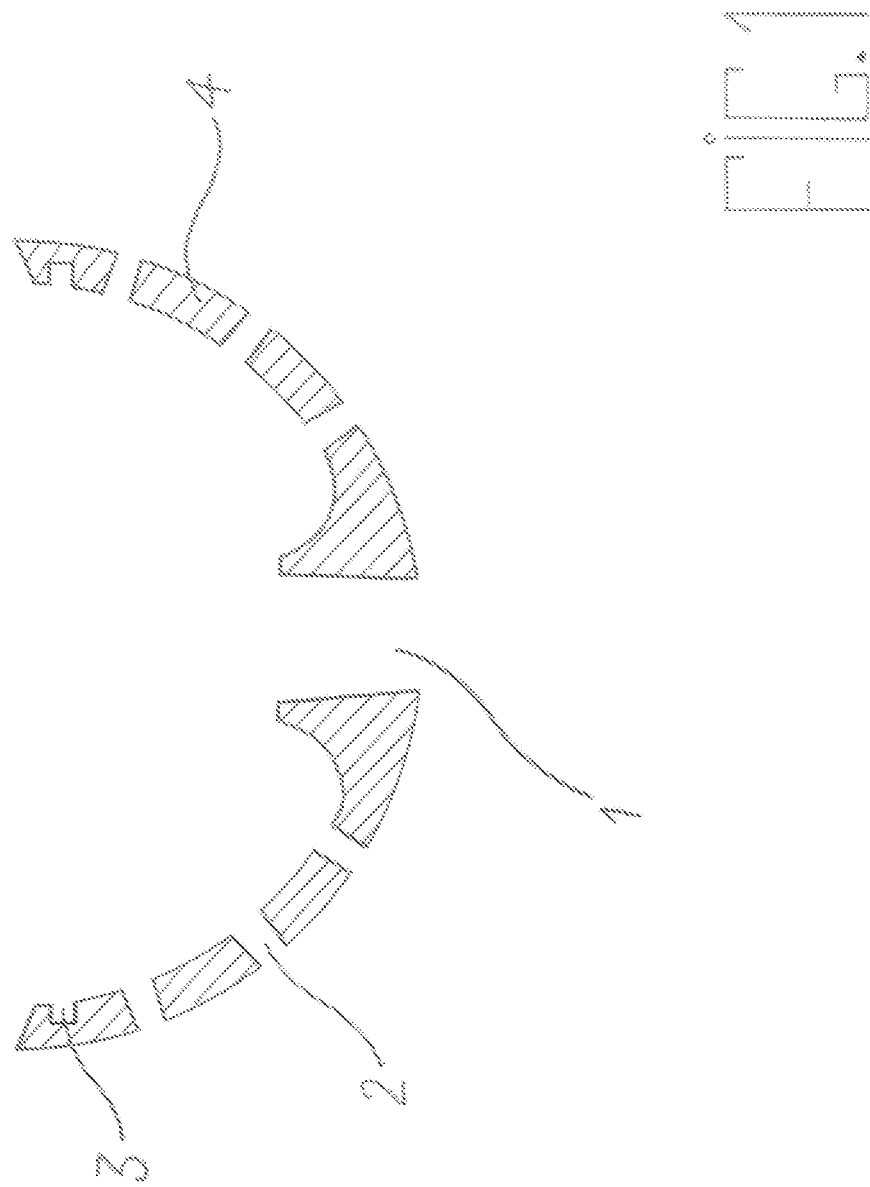
FIG. 1 is sectional view of the interlocking reverse hip acetabular cup with the central Morse tapered opening.
Figure 2:
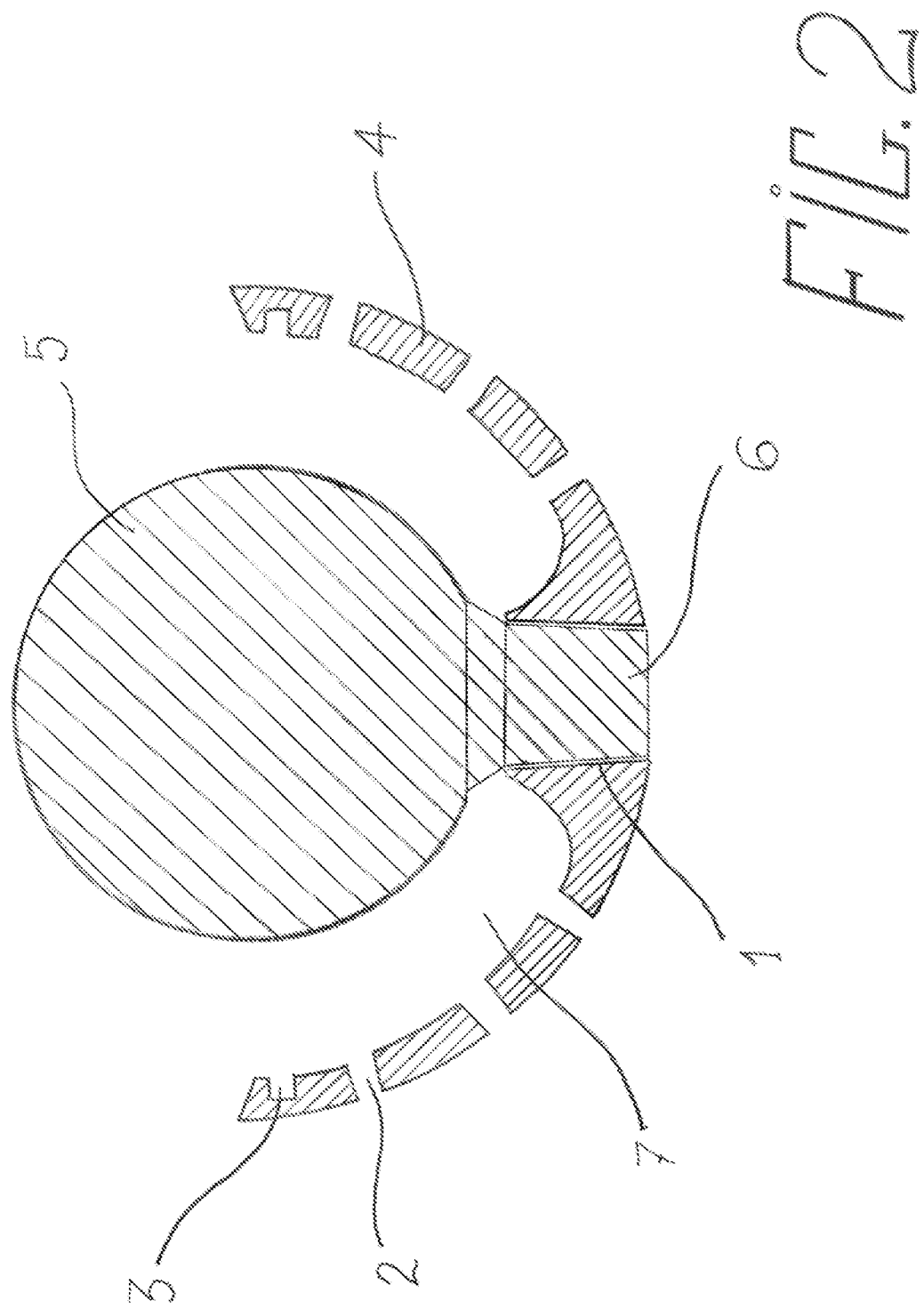
FIG. 2 is a cross sectional view of the interlocking reverse hip acetabular cup with central post inserted into the Morse tapered opening.
Figure 3:
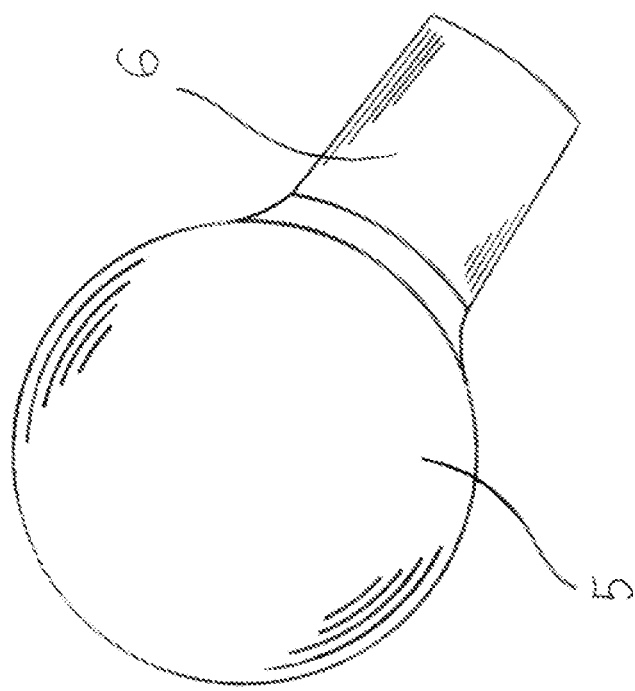
FIG. 3 is a perspective view of the monoblock acetabular ball and the tapered central post.

Turning now descriptively to the drawings, in which similar reference characters denote similar elements throughout the several views, the attached figures illustrate an interlocking reverse hip prosthesis, which comprises a hemispherical acetabular cup (4) having a smooth concave surface and a convex non-articulating surface. The convex non-articulating surface provides a porous surface with multiple asperities and micro-voids to allow bone ingrowth. Furthermore, the acetabular cup (4) provides one or more holes (2) at different locations for the purpose of using one or more interlocking screws (not shown). The concave hemispherical surface of the acetabular cup (4) provides a central female tapered opening (1) extended inside the concave space of the acetabular cup. Said opening is tapered to comfortably receive the male tapered central post (6). The acetabular ball (5) is firmly attached to the central post as a monoblock or it can be firmly attached using Morse taper.

In an embodiment, the acetabular cup provides at least two recesses (3) diametrically opposed situated close to the equatorial edge of the cup near the circumferential edge of the acetabular cup and used to secure the handheld impactor for impacting the cup into the acetabular pelvic cavity prepared by the operating surgeon.

In a different embodiment, the unitary acetabular may provide more then two recesses for receiving fixation pins. Furthermore, said recesses may have the shape of a square, or oval.

Figure 4:
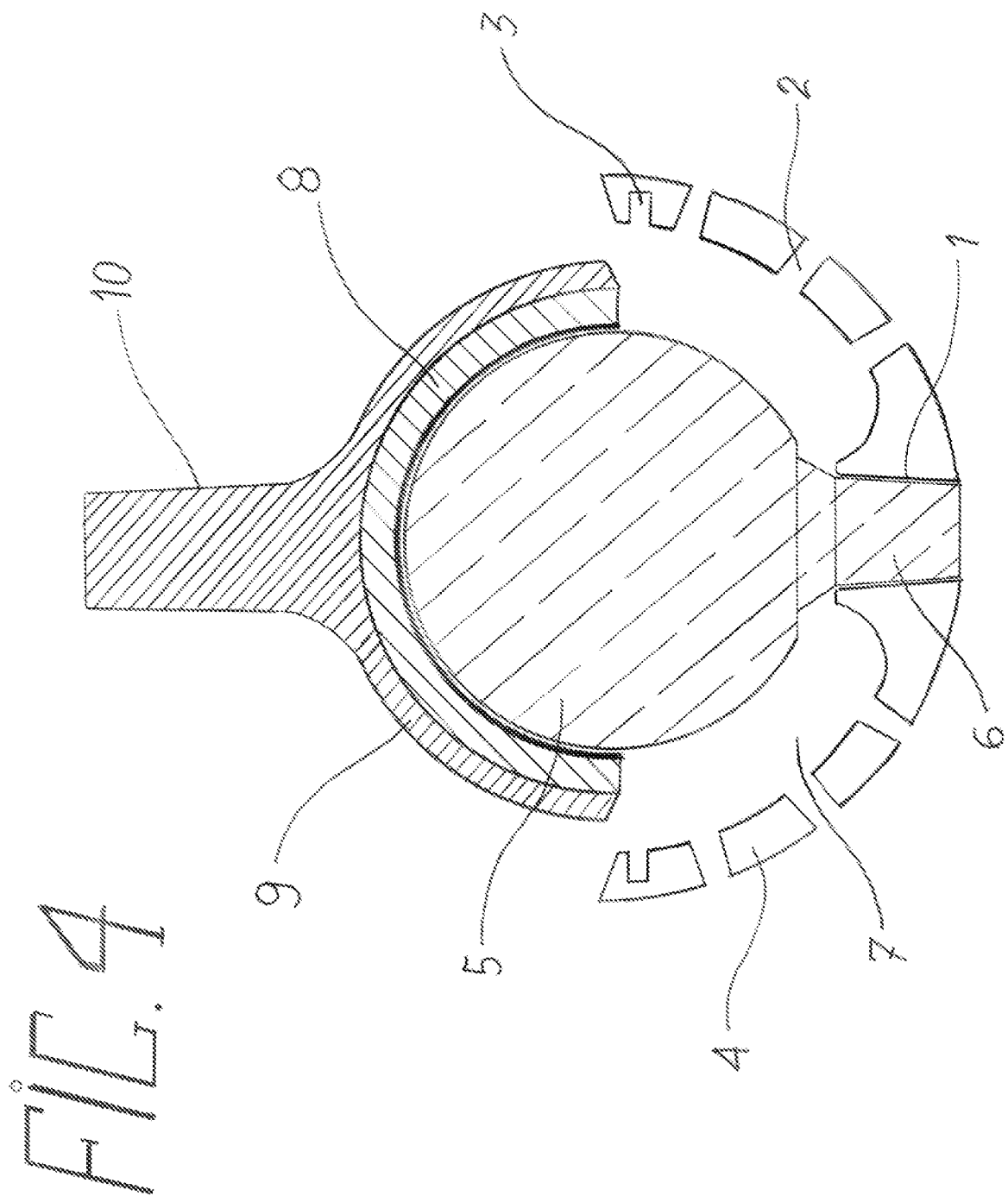
FIG. 4 is a cross sectional view of the assembled reverse interlocking hip implant.

FIG. 4) illustrates the acetabular cup having the acetabular ball and the central post (6) impacted into the central opening (1). The femoral metallic cup (9) having a tapered stem (10) and polyethylene lining (8) comfortably in contact with the acetabular ball (5).

In one embodiment, the articular surface of the femoral cup contains a high molecular weight polyethylene of varying thickness but no less than 4 mm. In a different embodiment the lining could be porcelain, ceramic, or metallic alloy. Variation of the design to meet different sizing needs will be apparent to those having skill in the art.

Referring to FIG. 4, when the metallic femoral cup 8 and its polyethylene lining 9 articulate on the acetabular ball 5, the edges of the femoral cup move into and out of the hemispherical interlocking space (7) and the articular surface of the femoral cup maintains the same area of contact with the acetabular ball over the entire range of motion. In other words, 100% of the articular contact area of the femoral cup is maintained over the entire range of motion.

Figure 5:
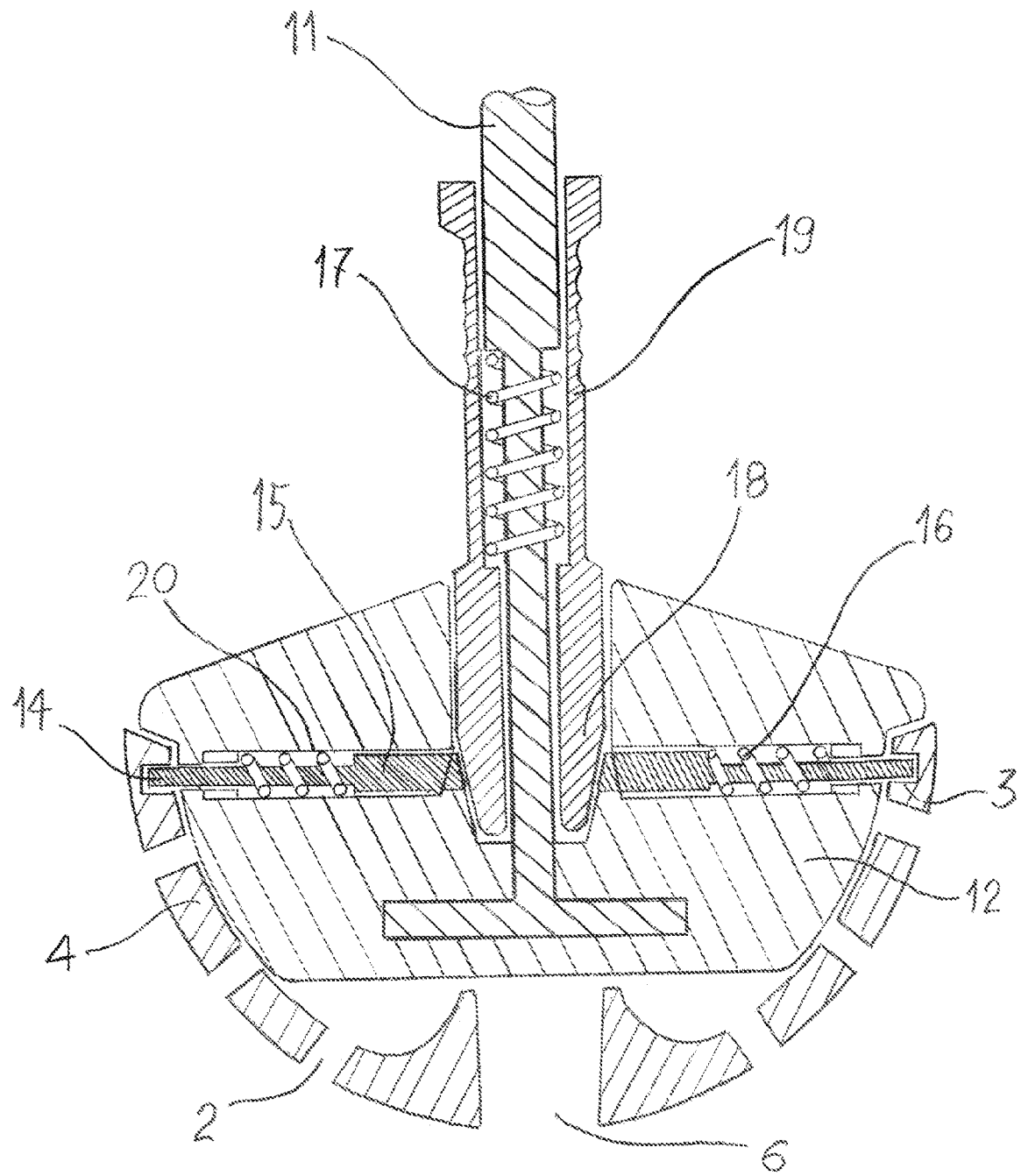
FIG. 5 is a cross sectional view of the acetabular cup impactor.

Referring now to FIG. 5 which describes in detail the acetabular cup handheld impactor. Said handheld impactor having a truncated hemispherical body (12) in form of a frustum and a lip extending beyond the circumference of the handheld impactor, thereby resting over the inclined rim of the acetabular cup. The distal surface of the hemispherical body does not contact the central Morse tapered central opening (6). A central shaft (11) extending upward, having a handle at its proximal end for impaction and distal end which is solidly embedded in the body of the polyethylene impactor (12). A metallic sleeve (19) situated around the central shaft (11) having a distal end in a form of a cone (18). Said sleeve is slidingly pushed distally via spring (17) situated in the space between the sleeve (19) and the central shaft (11). In order to maintain the acetabular cup securely attached to the impactor, two fixation pins are diametrically opposed and situated within channel (20) and remain retracted and pushed inward via spring (16). When sleeve (19) is pushed downward via spring (17), the distal cone (18) will push the fixation pins 14 into the acetabular cup recess (3) thereby securing the acetabular cup to the handheld impactor during the impaction process.

In another embodiment of the present invention the acetabular cup has multitude of holes for insertion of multiple fixation screws specifically designed for use in revision surgery of the hip.

Revisions are surgical procedures where the existing implant is removed. This most frequently requires removal of the acetabular cup and is associated with high levels of morbidity. The removal of a previously implanted acetabular cup may be quite difficult surgically, especially when the cup has metallic beads for bone ingrowth. In these cases, the removal is also associated with iatrogenic bone loss leading to difficulty in inserting another conventional acetabular cup.

An important feature of the present invention is the ability to place the acetabular cup in position and impact it without having the central post interfere with the placement of the multiple screws at different angles, such as during revision surgery. Subsequent to the acetabular cup insertion, the central post and acetabular ball will be appropriately impacted into the central Morse taper. As mentioned above, there is a significant advantage to using multiple screws during revision hip surgery where the quality of acetabular bone dictates the number and position of the fixation screws. Having a central post will limit the exposure and interfere with the placement of said fixation screws.

It is, therefore, the object of the present invention to provide a new and improved interlocking reverse hip prosthesis system where the metallic acetabular cup provides a removable central post allowing the insertion of a multitude of fixational screws such as during revision hip surgery or complicated fracture cases requiring reconstruction of the pelvic bone.

With respect to the above description, it is to be realized that the optimum dimensional relationship for the parts of the invention, to include variations in size, material, shape, form, function, manner of operation, assembly, and use, are deemed readily apparent to the skilled in the art, and all equivalent relationships to those illustrated in the drawings and described in the specification are intended to be encompassed by the present invention. Therefore, the foregoing is considered as illustrative only of the principle of the invention. Furthermore, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A reverse hip prosthesis system comprising:
   a unitary acetabular cup having a convex non-articulating surface for attachment to an acetabular socket in a pelvic bone and a concave surface located opposite to the convex non-articulating surface, the concave surface having a central opening said central opening providing a female Morse taper adapted to receive a peg having a corresponding male Morse taper;
   an inner circular wall having a narrow end and a larger end, wherein the larger end extends inside the concave space of the unitary acetabular cup;
   an outer peripheral sidewall that flares out to seamlessly continue with the concave surface;
   an acetabular ball firmly attached to said peg, the peg being configured to lock within said female Morse taper early enough to prevent the acetabular ball from making direct contact with the outer peripheral sidewall or the concave surface of the unitary acetabular cup;
   a femoral cup to be firmly affixed to a proximal end of a femoral implant; and
   a handheld impactor for inserting the acetabular cup into a prepared acetabular bony cavity.

2. The reverse hip prosthesis system of claim 1 wherein the concave surface of the acetabular cup is hemispherical.

3. The reverse hip prosthesis system of claim 1 wherein the inner circular wall height, measured from the narrow end to the larger end, does not to exceed one and half the diameter of the larger end central opening.

4. The reverse hip prosthesis system of claim 3 wherein said unitary acetabular cup provides at least two or more recesses configured for receiving fixation pins from said handheld impactor.

5. The reverse hip prosthesis system of claim 4 wherein said at least two or more recesses are diametrically opposed and are located close to the equatorial edge of the cup.

6. The reverse hip prosthesis system of claim 5 wherein the two or more diametrically opposed recesses are circular pinholes, oblong, or polygonal in shape.

7. The reverse hip prosthesis system of claim 6 wherein said handheld impactor comprises:
   a metallic sleeve; mounted on a central shaft, the shaft providing a handle at its proximal end;
   a spring mounted on said central metallic core for distally biasing said metallic sleeve; and
   a polyethylene frustum for preventing contact with a central Morse extension during impaction, said polyethylene frustum having at least two or more diametrically spring-loaded fixation pins.

8. The reverse hip prosthesis system of claim 7 wherein the distal end of said metallic sleeve is tapered in order to provide a cam action which extends the fixation pins outwardly into the diametrically opposed recesses of the unitary acetabular cup.

9. The reverse hip prosthesis system of claim 7 wherein said fixation pins are located in diametrically opposed cylindrical channels and pushed inwardly via springs.

10. The reverse hip prosthesis system of claim 9 wherein said springs are coil springs.

11. The reverse hip prosthesis system of claim 1 where in the convex surface of the acetabular cup is hemispherical.

12. The reverse hip prosthesis system of claim 1 wherein handheld impactor device is fabricated from metal, metallic alloy, or composite material.

* * * * *